United States Patent
Phillips

(10) Patent No.: US 10,406,357 B2
(45) Date of Patent: *Sep. 10, 2019

(54) VENOUS ELECTRICAL STIMULATION APPARATUS AND METHODS AND USES THEREOF

(71) Applicant: NOVINTUM MEDICAL TECHNOLOGY GMBH, Schaffhausen (CH)

(72) Inventor: David Bruce Phillips, Waterford, VA (US)

(73) Assignee: NOVINTUM MEDICAL TECHNOLOGY GMBH, Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/122,754

(22) Filed: Sep. 5, 2018

(65) Prior Publication Data

US 2019/0009088 A1    Jan. 10, 2019

Related U.S. Application Data

(63) Continuation of application No. 14/917,745, filed as application No. PCT/US2014/055551 on Sep. 15, 2014, now Pat. No. 10,092,752.
(Continued)

(51) Int. Cl.
*A61N 1/36*    (2006.01)
*A61N 1/04*    (2006.01)
*A61M 5/42*    (2006.01)

(52) U.S. Cl.
CPC ......... *A61N 1/36014* (2013.01); *A61M 5/422* (2013.01); *A61N 1/0456* (2013.01);
(Continued)

(58) Field of Classification Search
CPC .......................... A61N 1/36014; A61N 1/0456
(Continued)

(56) References Cited

U.S. PATENT DOCUMENTS

| 3,872,859 A | 3/1975 | Pitzen et al. |
| 4,459,988 A | 7/1984 | Dugat |

(Continued)

FOREIGN PATENT DOCUMENTS

| CN | 1842356 | 10/2006 |
| JP | 2008520306 | 6/2008 |

(Continued)

OTHER PUBLICATIONS

Broderick et al., "A pilot evaluation of a neuromuscular electrical stimulation (NMES) based methodology for the prevention of venous stasis during bed rest," Medical Engineering & Physics, May 2010, vol. 32(4), pp. 349-355.

(Continued)

*Primary Examiner* — Nadia A Mahmood
(74) *Attorney, Agent, or Firm* — McDermott Will & Emery LLP

(57) ABSTRACT

An electrical venous stimulation apparatus comprising an electrical signal generator, the signal generator configured to generate a specified electrical output signal. The apparatus also includes a plurality of electrodes in electrical communication with the signal generator and configured to be placed in electrical communication with a subject. The electrical output signal sent to the subject includes an output voltage, electrical current, and waveform that changes with time in a preprogrammed repeating cycle. The output voltage, electrical current, and waveform are configured to elicit a physiological response that stimulates a plurality of peripheral nerves in the subject, activates a venous muscle pump mechanism in one or more limbs of the subject, and
(Continued)

non-invasively alter the physiology of target vein(s), wherein the target vein(s) is caused to distend from under the surface of the subject's skin.

36 Claims, 9 Drawing Sheets

Related U.S. Application Data

(60) Provisional application No. 61/878,869, filed on Sep. 17, 2013.

(52) U.S. Cl.
CPC ......... *A61N 1/0472* (2013.01); *A61N 1/0492* (2013.01); *A61N 1/0476* (2013.01)

(58) Field of Classification Search
USPC ...................................... 607/52, 72
See application file for complete search history.

(56) References Cited

U.S. PATENT DOCUMENTS

| | | |
|---|---|---|
| 4,846,181 A | 7/1989 | Miller |
| 4,846,185 A | 7/1989 | Carim |
| 5,312,350 A | 5/1994 | Jacobs |
| 5,562,718 A | 10/1996 | Palermo |
| 5,725,563 A | 3/1998 | Klotz |
| 6,615,080 B1 | 9/2003 | Unsworth et al. |
| 8,118,750 B2 | 2/2012 | Gerber |
| 8,165,685 B1 | 4/2012 | Knutson et al. |
| 8,175,713 B1 | 5/2012 | Cywinski |
| 2004/0267333 A1 | 12/2004 | Kronberg |
| 2005/0149124 A1 | 7/2005 | Brogan et al. |
| 2005/0234525 A1 | 10/2005 | Phillips |
| 2006/0253165 A1 | 11/2006 | O'Kelly |
| 2007/0270917 A1 | 11/2007 | Nachum |
| 2009/0156958 A1 | 6/2009 | Mehta |
| 2009/0177184 A1 | 7/2009 | Christensen |
| 2011/0082517 A1 | 4/2011 | Brezel |
| 2011/0178572 A1 | 7/2011 | Czyrny |
| 2012/0088986 A1 | 4/2012 | David |
| 2012/0215137 A1 | 8/2012 | Zanelli |

FOREIGN PATENT DOCUMENTS

| | | |
|---|---|---|
| JP | 2011045562 | 3/2011 |
| WO | 199927991 | 6/1999 |

OTHER PUBLICATIONS

Cabric, M., et al., "Stereological Analysis of Capillaries in Electrostimulated Human Muscles," Int. J. Sports Med,. vol. 8 (5), Oct. 1987, 327-330.

Canadian Office Action for Application No. 2,923,890, dated Oct. 30, 2018, 6 pages.

VENOUS ELECTRICAL STIMULATION APPARATUS AND METHODS AND USES THEREOF

This application is a continuation of U.S. patent application Ser. No. 14/917,745, filed on Mar. 9, 2016, which is a National Stage entry and claims priority to International Application No. PCT/US2014/055551, filed on Sep. 15, 2014, which claims priority to U.S. Provisional Patent Application No. 61/878,869, filed on Sep. 17, 2013, the contents of which are hereby incorporated by reference in their entirety.

TECHNICAL FIELD

This disclosure relates to medical devices for providing improved venous access to aid in the drawing of blood from, administering fluids or drugs via, or insertion of a peripheral intravenous cannula into, the veins of a patient.

BACKGROUND

The single standard practice for gaining peripheral venous access in a medical patient has not changed significantly in over 80 years. Typically, the standard practice involves the use of a tourniquet applied to an upper portion of a patient's arm. The application of a tourniquet stops the flow of blood to the heart and allows whatever pressure is available from the arteries and capillaries to fill and distend the veins. A medical practitioner, such as a doctor, physician's assistant, paramedic, or nurse, may then access the distended vein with a needle to draw blood, or insert a peripheral venous catheter or other such cannula into the distended vein to administer drugs or other fluids. This is a painful, sometimes dangerous, time consuming, and inaccurate method.

In a majority of patients, this approach is sufficient for either the drawing of blood for hematology analysis, or for the placement of an intravenous cannula to administer fluids, including but not limited to volume expanders (e.g., colloids (e.g., blood, dextran, hydroxyethyl starch, stroma-free hemoglobin), crystalloids (e.g., normal saline, Ringer's Lactate, glucose/dextrose, Hartmann's Solution), blood-based products (e.g., red blood cells, plasma, platelets), blood substitutes (e.g., oxygen-carrying substitutes), buffer solutions (e.g., intravenous sodium bicarbonate, Ringer's Lactate), nutritional formula (e.g., peripheral parenteral nutrition), or drugs including but not limited to antibiotics, analgesics or chemotherapy into the blood stream of a patient. However in most patients, geriatric patients or cancer treatment patients for example, gaining venous access can be difficult and problematic for any number of reasons, which may lead to medical practitioners requiring multiple repeated attempts to successfully gain intravenous access to the patient's vein(s). Repeated attempts, to gain venous access in a patient may result in a variety of adverse issues including hematomas, fluid infiltration into the surrounding tissue (which, with chemotherapy agents, can cause severe local reactions), pain, shock, discomfort, vasoconstriction, and in emergency situations, may require the practitioner to switch to either a central venous access approach or a "cut-down" (opening the tissue) to gain access to a vein.

There are many types of patients in whom these problems can result. Elderly or geriatric patients frequently have frail veins or are peripherally shut down due to dehydration. Pediatric and neonatal (newborn) patients are especially difficult to gain venous access to, due to small veins and the significant immaturity of their bodies. Patients who have lost blood volume through trauma, shock, or dehydration (such as ER and paramedic patients, patients injured in road traffic accidents or military combat, crush victims, famine victims, etc.) are likely to be peripherally shut down, making it difficult to locate and raise a vein, but are often the patients in whom medical practitioners most rapidly need to gain venous access. Obese patients are yet another patient group in which medical practitioners encounter difficulties in locating or raising a vein for venous access. Cancer treatment patients also present difficulties for medical practitioners to gain venous access due to, among other things, phlebitis.

Other methodologies and devices have been employed to attempt to locate target veins for venipuncture or determine when a proper and successful venipuncture has been achieved. However, such devices and methodologies are either passive and non-invasive devices and techniques, or they are invasive mechanical devices and techniques that actually first require the puncture of the target vein in order to determine the position of the needle within the vein (which does not otherwise aid in locating the target vein or increasing the ease of inserting the needle into the target vein). One example of a passive technique and device is the use of a strong source of visible or ultraviolet light placed against the skin of the patient in an attempt to read the reflectivity of the underlying iron in the patient's red blood cells in the target vein, through the patient's skin. While this passive technique may help to locate a target vein, it does not increase the ease of achieving successful venipuncture. Additionally, the vein will often roll away from the needle when the medical practitioner tries to inset it. The drawback to using active mechanical devices that need to puncture the lumen to determine the position therein is that, if the machine performing the venipuncture goes too far and pushes the needle completely through the opposite side of the target vein, the result is a double penetration of the vein requiring the tip of the needle to be withdrawn back into the lumen of the vein. Accordingly such mechanical techniques are flawed in that they permit the possibility of a double penetration which may result in blood leaking from the second vein puncture causing a hematoma in the patient.

Accordingly, there is a need for a more rapid, reliable, less painful, more efficient, safer, and repeatable method of distending a patient's veins in the hands, arms, feet, or legs to allow easier venous access by medical practitioners. In addition, there is a need for a medical apparatus that can cause a more rapid, reliable, and repeatable distension or expansion of veins in a patient's hands, arms, feet or legs across a broader patient spectrum including geriatric, pediatric, neonatal, and trauma patients, to assist medical practitioners in gaining venous access.

SUMMARY

In general terms, this disclosure is directed to electrical venous stimulation. In one possible configuration and by non-limiting example, the electrical venous stimulation is used to provide improved access to a vein. Various aspects are described in this disclosure, which include, but are not limited to, the following aspects.

One aspect is an electrical venous stimulation apparatus, for causing target veins in a subject to distend from under the surface of the subject's skin, comprising: a power supply, a signal generator powered by the power supply, the signal generator configured to generate a specified electrical output signal, and a plurality of electrodes in electrical communication with the signal generator and configured to be placed in electrical communication with the subject, wherein the electrical output signal includes an output voltage, electrical current, and waveform that changes with time in a preprogrammed repeating cycle, the output voltage, electrical current, and waveform being configured to elicit a physiological response that stimulates a plurality of peripheral nerves in the subject, activates a venous muscle pump mechanism in one or more limbs of the subject, and non-invasively alter the physiology of a target vein, wherein the target vein is caused to distend under the surface of the subject's skin.

Another aspect is a method of stimulating peripheral target veins to cause the veins to distend under the surface of a subject's skin to facilitate venipuncture, comprising: generating an adjustable electrical output signal with an electrical venous stimulation apparatus, the signal including an adjustable output voltage, an adjustable current, and an adjustable output voltage waveform configured to elicit a physiological venous response in the subject that causes the target vein in the subject to distend under the surface of the subject's skin, the electrical stimulation apparatus including, a powered signal generator configured to generate the adjustable electrical signal, and a plurality of electrodes in electrical communication with the signal generator and configured to be placed in electrical communication with the subject; and transmitting the output signal to the subject via the plurality of electrodes.

A further aspect is a method of suppressing pain signals at a venous needle stick site of a subject, comprising: generating an adjustable electrical output signal with an electrical venous stimulation apparatus, the signal including an adjustable output voltage, an adjustable current, and an adjustable output voltage waveform configured to elicit a physiological venous response in the subject that causes the target vein in the subject to distend under the surface of the subject's skin, the electrical stimulation apparatus including, a powered signal generator configured to generate the adjustable electrical signal, and a plurality of electrodes in electrical communication with the signal generator and configured to be placed in electrical communication with the subject; and transmitting the output signal to the subject via the plurality of electrodes, and thereby stimulating the peripheral nerves and activating the venous pump mechanism in at least one limb of the subject.

A further aspect is a method of accessing a vein of a person, the method comprising: receiving a portion of a limb of the person into a container; supplying a liquid electrolytic solution into the container, wherein the liquid electrolytic solution is in contact with the portion of the limb; electrically stimulating the portion of the limb with at least one signal generated by an electrical signal generator, the electrical signal provided to the electrolytic solution by at least one electrode in contact with the liquid electrolytic solution; causing at least one vein in the limb of the person to distend in response to the electrical stimulation; and inserting a tip of a needle into the vein while it is distended to access the vein.

Another aspect is a venous electrical stimulation apparatus for temporarily enlarging and distending the peripheral veins in the limbs of a patient to make it easier for a medical practitioner to gain venous access when drawing blood or when inserting an intravenous cannula, such as a catheter, into the vein. The venous electrical stimulation apparatus is configured to stimulate one or more muscles that form an anatomical part of the vein to cause the circumference of the vein's lumen to enlarge, thus making the target vein press against the skin, and simultaneously creating a vacuum in the target vein that can help increase the total volume of blood within the vein, which also helps make it easier and safer to perform venipuncture.

Yet another aspect is an apparatus that includes a signal generator having a pair of electrical output terminals, a power supply in electrical communication with the signal generator, at least a pair of electrical leads in electrical communication at a proximal end with the output terminals of the signal generator, and at least a pair of electrodes in electrical communication with the proximal ends of the leads, and configured to introduce the electrical signal into a patient (or subject). The patient or subject can be a mammal, and more specifically, a human.

In another aspect the apparatus is configured to non-invasively alter the physiology of the peripheral veins that are targeted for venipuncture in the limbs of a patient using an active electrical signal, rather than using passive means traditionally used or requiring the use of a tourniquet. In an aspect of the present disclosure, an active signal imparted to the skip of a patient by the apparatus elicits a physiological response and a change in condition/behavior of the target vein, causing the vein to fill with blood and become distended/enlarged and become more rigid, therefore increasing the visibility of the vein through the skin. In this manner, using such an apparatus and methodology, it becomes easier for medical practitioners to achieve successful and proper venipuncture. No other active device currently exists that non-invasively changes the physiology of the tissue in and around the target veins to aid in locating the target vein and increasing the ease of achieving successful and proper venipuncture without the need for multiple attempts.

In yet another aspect, the electrical signal generator includes a plurality of capacitors and resistors, and at least one potentiometer for adjusting the output voltage. The electrical signal generator further includes programming configured to adjust the output signal, which may include one or more of the output voltage, output current, output voltage waveform, and/or signal frequency that is imparted to the patient over time, to stimulate the venous pump action in the motor muscles of the patient's limbs resulting in distension of the peripheral veins of a patient. In one embodiment, the electrical signal generator is configured to change the output voltage and the shape of the output voltage waveform. The output voltage determines how many muscle fibers are recruited and fired (i.e. the muscle stimulation portion of the waveform), as well as how much energy is used to fire the nerve impulses across the synaptic junction. The shape of the output voltage waveform determines what information is communicated to the brain.

In another aspect, the electrical signal generated is an AC signal of less than one milliamp and the output voltage from the potentiometer is in the range of 0 to 90 volts.

In another aspect, the electrical signal generator generates a specific predefined output voltage waveform that is imparted to the skin overlying the limbs of the patient. One portion of the generated electrical waveform is specifically tuned to the frequency, duty cycle, pulse width, and voltage at which the tiny muscles surrounding the target veins exhibit a physical response, resulting in muscular expansion and contraction. This predefined waveform and the resulting response in the veins makes them rigid and enlarges their circumference. Another portion of the predefined waveform stimulates the nearby nerves in the skin to override any pain signals in the body resulting front the needle stick. This nerve stimulation reduces the pain and anxiety usually accompanying a venipuncture. Still another portion of the electrical signal stimulates the brain to release endorphins to the body, thereby reducing anxiety in the patient.

In another aspect of the present disclosure is a method of providing medical practitioners with peripheral venous access in patients while suppressing pain signals at a venous needle stick site by stimulating the peripheral nerves and activating the venous pump mechanism in the limbs of a patient using an external electrical stimulation apparatus, thereby causing the peripheral nerves to distend and become more visible under the surface of the skin.

In another aspect, for non-emergency patients, one benefit to using some embodiments disclosed herein is the reduction of the time spent by medical practitioners acquiring venous access and the reduction of the number of failed attempts at venous access in patient groups whom medical practitioners historically have had difficulties gaining venous access. Furthermore, in emergency situations and for emergency patients, having the ability to gain rapid venous access can increase the speed with which vital fluids and/or drugs may be administered, thereby potentially saving vital minutes and patient lives.

BRIEF DESCRIPTION OF THE DRAWINGS

The figures are for illustration purposes only and not necessarily drawn to scale. However, the present disclosure may be best understood by reference to the detailed description which follows when taken in conjunction with the accompanying drawings.

DETAILED DESCRIPTION

Figure 1:
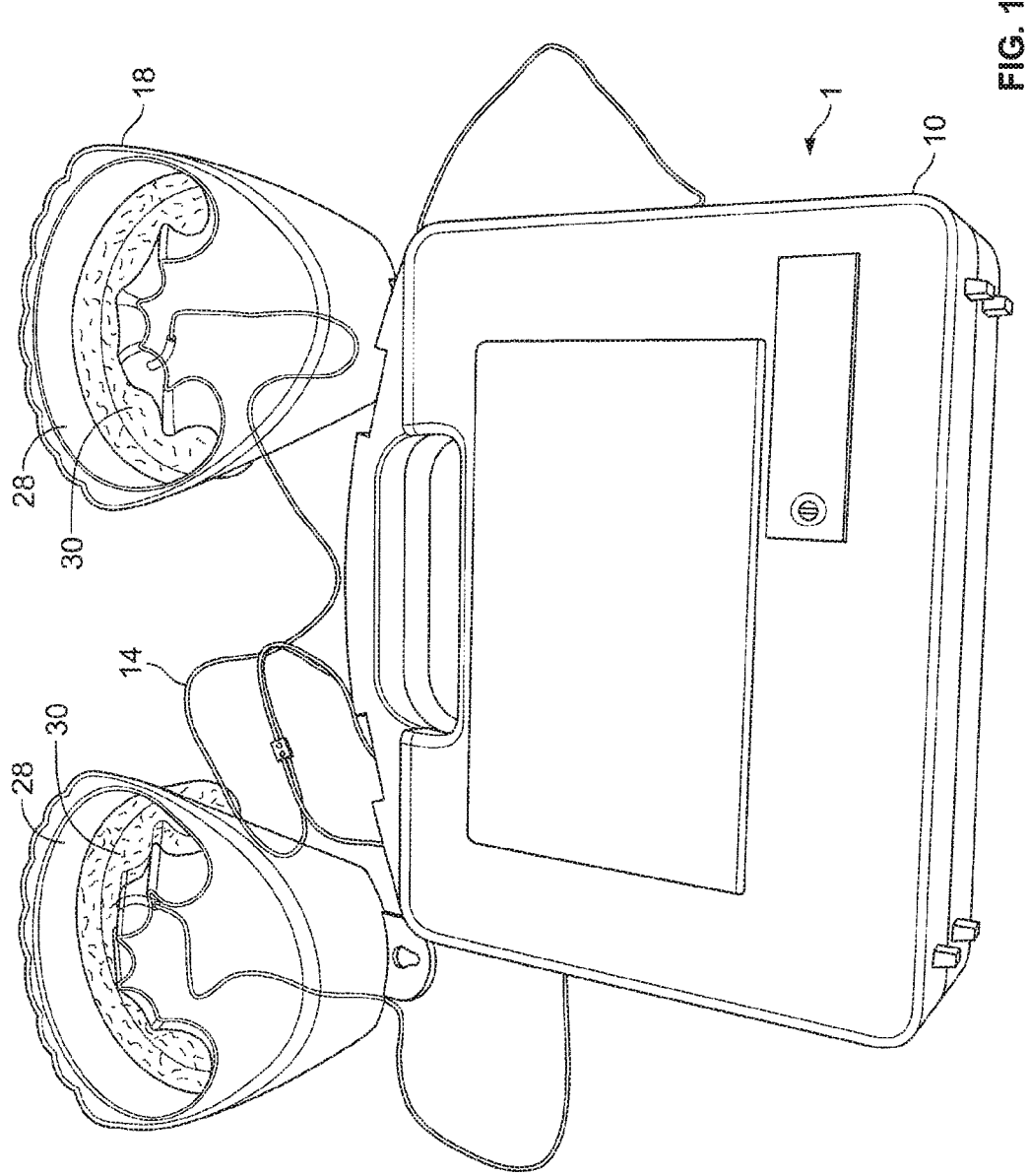
FIG. 1 is a top front isometric view of an example embodiment of an electrical vein stimulation and expansion apparatus of the present disclosure.
Figure 2:
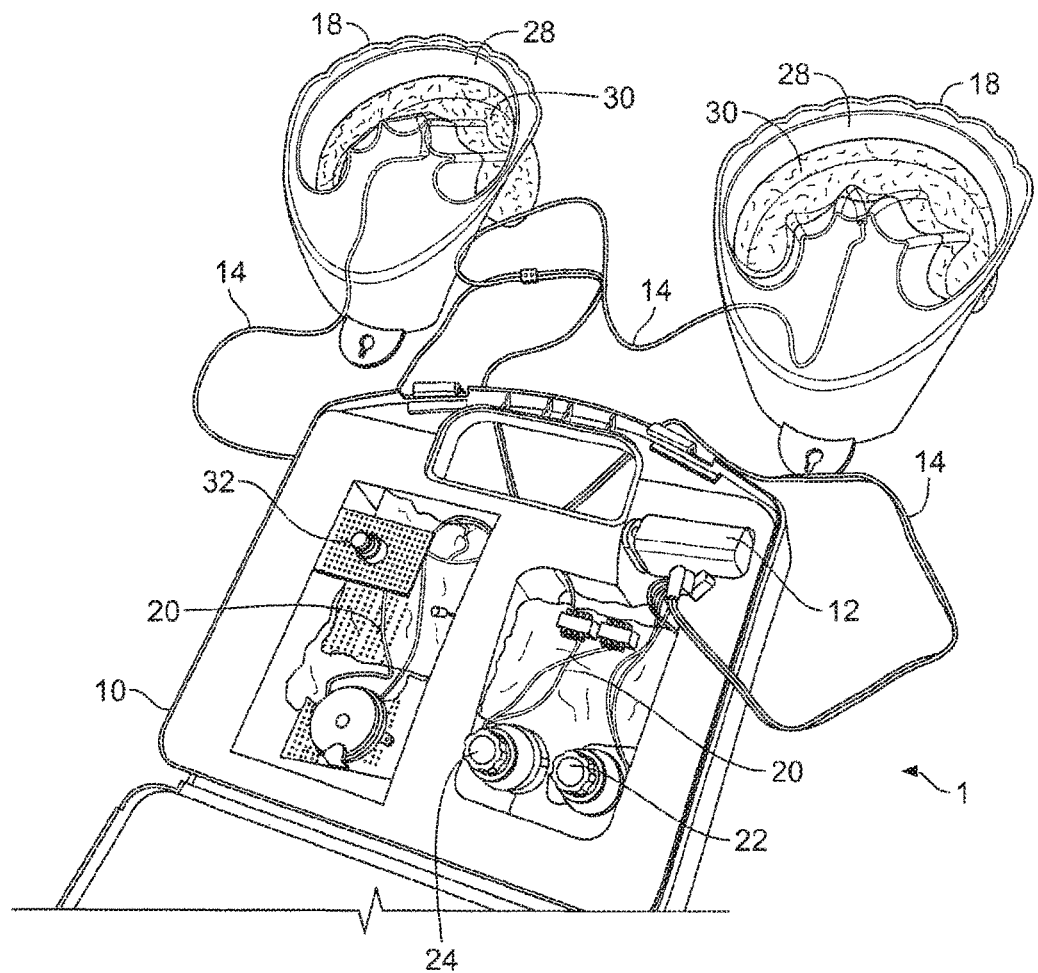
FIG. 2 is a top isometric view of the electrical vein stimulation and expansion apparatus of FIG. 1, showing the cover of the electrical signal generator in an open position to expose the internal circuitry and electrical components of the example electrical signal generator.
Figure 3:
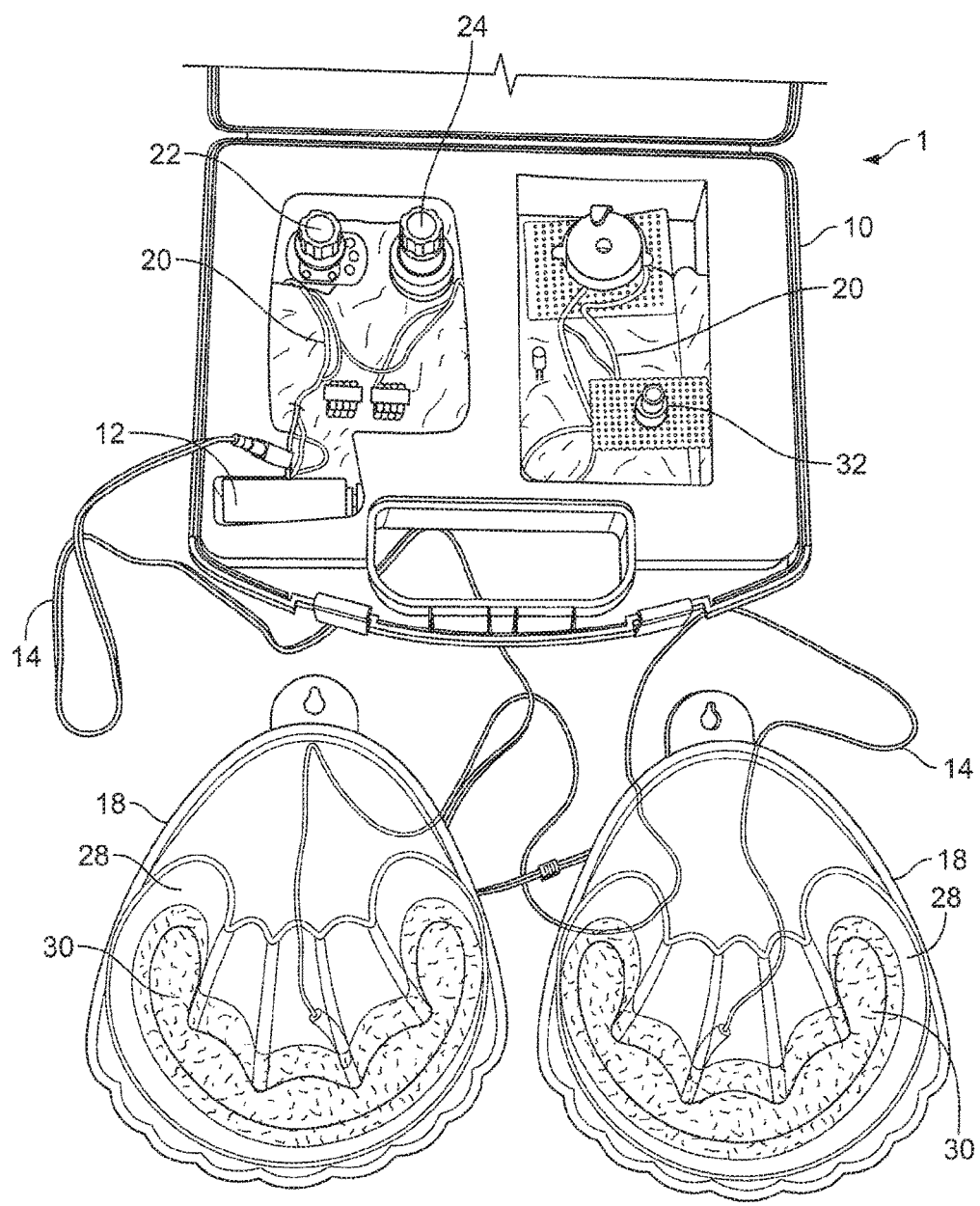
FIG. 3 is another top isometric view of the electrical vein stimulation and expansion apparatus of FIG. 1.
Figure 4:
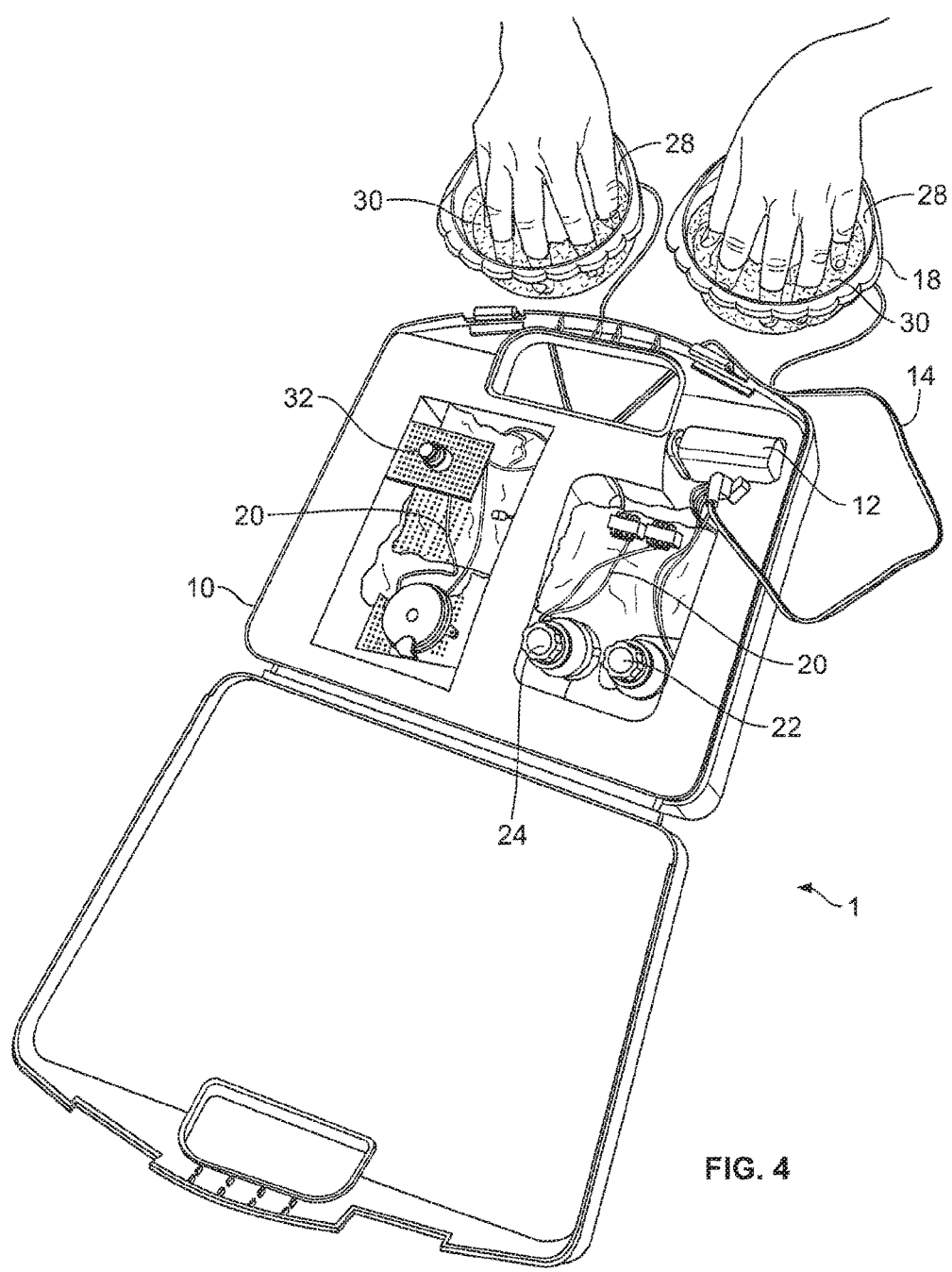
FIG. 4 is another top front isometric view of the electrical vein stimulation and expansion apparatus of FIG. 1, showing the apparatus ready for use wherein a patient has her fingertips placed in containers of electrolyte solution that are electrically connected to the signal generator of the apparatus.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

While the present disclosure is capable of embodiment in various forms, there is shown in the drawings, and will be hereinafter described, one or more presently preferred embodiments with the understanding that the present disclosure is to be considered as an exemplification of the invention, and is not intended to limit the invention to the specific embodiments illustrated herein. Headings are provided for convenience only and are not to be construed to limit the invention in any way. Embodiments illustrated under any heading may be combined with embodiments illustrated under any other heading.

Referring to FIGS. 1-5, in general, disclosed herein is an electrical stimulation apparatus 1 configured to deliver an electrical signal through the arms or other limbs of a patient and cause the veins in the hands and/or arms of the patient to distend or expand and thereby become more visible under the surrounding surface of the skin. Such signals can be delivered directly to one limb; up one limb, up through the limb, across the spine, and/or down through the other limb, for example. In doing so, the stimulation apparatus makes the peripheral veins in the arms or hands of the patient more visible, thereby providing a medical practitioner venous access for the drawing of blood or the insertion of a peripheral venous cannula. The apparatus is generally placed in electrical communication with a patient's hands and/or arms (or other limbs) by a pair of electrodes or other electrical signal delivery device, that connects the device to the patient's arms to deliver a predetermined electrical signal through the electrically connected limbs of the patient.

The veins thus become filled with blood while being subjected to the electrical stimulation, increasing the internal pressure within the veins. The increased pressure in the veins makes them more rigid, thereby increasing the physical resistance, or force, required to insert a needle or other intravenous cannulas therein. The increased physical resistance of the target vein permits the medical practitioner to have an improved physical feel for the insertion of the needle into the vein, and to better differentiate instances when the tip of the needle has been correctly inserted into the central lumen of the vein, from instances in which the needle has pierced through the vein (which can cause serious medical complications).

In general, the electrical stimulation apparatus 1 comprises an electrical signal generator 10, a power supply 12 in electrical communication with the signal generator and configured to supply power thereto, at least a pair of electrical leads 14 connected at a proximal end to a plurality of electrical output terminals 16 of the electrical signal generator, and at least a pair of electrodes 18 connected to a distal end of each of the electrical leads 14.

The electrical power supply 12 may be a portable power supply, such as for example a 9-volt battery, other voltage battery, or rechargeable battery. Alternatively, the power supply may utilize a standard electrical power cord that plugs into a typical power outlet in a wall.

Figure 6:
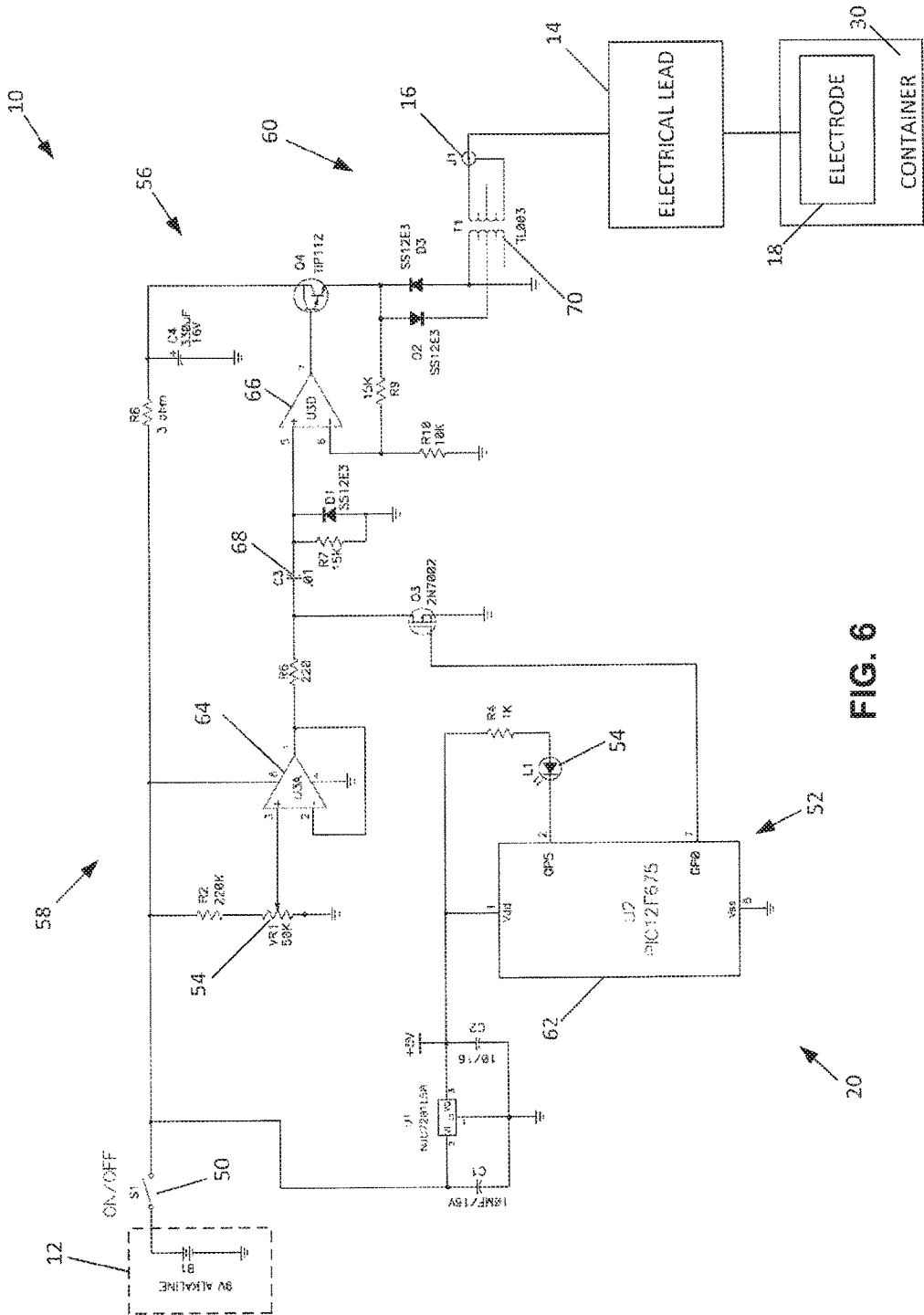
FIG. 6 is an electrical schematic of an embodiment of a signal generator of the electrical vein stimulation and expansion apparatus of the present disclosure.

An example of the electrical signal generator 10 is shown in FIG. 6. Also shown in FIG. 6 are the power supply 12, electrical lead 14, container 28, and electrolytic solution 30. Some embodiments include two or more electrical signal generators 10, coupled to one or more leads 14, electrodes 18, and containers 28.

The electrical signal generator 10 comprises electronic circuitry 20 operable to generate an electrical output signal, such as having one of the waveforms illustrated and described with reference to FIGS. 7-9, or another suitable waveform. In some embodiments the electronic circuitry 20 includes electronics such as one or more of resistors, capacitors, transformers, and a microprocessor in electrical communication with each other. In the example shown in FIG. 6, the electronic circuitry 20 of the electrical signal generator 10 includes a power switch 50, oscillator 52, variable control 54, and output circuitry 56. In this example the oscillator 52 includes an integrated circuit, such as a microcontroller 62. The output circuitry 56 includes a first stage 58, such as including operational amplifiers 64 and 66 and capacitor 68, and a second stage 60, including transformer 70. The output of the second stage 60 forms the output terminal 16, which can be electrically coupled to the lead 14 and electrode 18, to deliver the output signal to the patient.

The oscillator 52 operates to generate an initial oscillating signal. In this example, the oscillator includes a square wave generator. One example of a square wave generator is a microcontroller, such as the 8-pin, flash-based 8-bit CMOS microcontroller, part number PIC12F675 available from Microchip Technology Inc. of Chandler, Ariz., US. Another example of a square wave generator is a 555 timer. The square wave generator produces a squarewave signal, which oscillates between low and high voltages, such as between 0 and 5 volts. In this example the square wave has a frequency in a range from 4 Hz to 12 Hz. As one example the frequency is 7.83 Hz. Frequencies in this range have been found to be preferred over faster frequencies because they give the nerves in the patent time to repolarize after stimulation before the next stimulation. The frequency can be higher for a healthy person whose nerves can repolarize more quickly, while the frequency typically needs to be lower for an unhealthy person whose nerves require more time to repolarize.

In some embodiments the signal generator 10 includes a variable control 54, such as one or more potentiometers 22, 24 in electrical communication with the electronic circuitry of the signal generator 10. The one or more variable controls 54 allow an operator, such as a medical practitioner, the patient, or another person to provide an input to adjust the magnitude of the signal generated by the signal generator 10, such as to increase or decrease the magnitude of the signal. In this example, each potentiometer 22, 24 that is present in the signal generator corresponds to a separate output voltage channel (each having its own signal generator 10) having its own leads 14 and electrodes 18, and whose voltage is adjusted by its own intensity adjustment knob coupled to the variable control 54 that adjusts/sets the output voltage of that channel that is sent from the signal generator 10 to the patient via the leads 14 and electrodes 18. The ability to adjust the output voltage experienced by the patient allows a patient to have the voltage adjusted down to a comfortable level, which therefore contributes to lowering the patient's anxiety over use of the device, which thus reduces the chance of any anxiety or stress induced vasoconstriction that can reduce the amount of blood within the targeted veins.

In one embodiment, the signal generator 10 includes two variable controls (e.g., potentiometers 22, 24), and therefore may have two separate output voltage channels each having its own signal generator 10, with each intensity knob and variable control 54 separately adjusting the output voltage to be sent to the patient along two sets of electrodes, corresponding to each of the two output voltage channels. A first of the two potentiometers 22 and its respective output voltage channel impart an output voltage to the patient that is configured to cause the target vain to become swollen or distended. A second of the two potentiometers 24 and its respective output voltage channel impart an output voltage to the patient that is configured to stop the pain at the needle stick site by interrupting nerve signals associated with pain. In the present embodiment, the two output voltage channels are identical, but in alternate embodiments, each potentiometer may be configured to adjust the output voltage in differing ranges. Having two separate channels, each with the ability to adjust the output voltage, allows the stimulation apparatus 1 to be configured to adapt to target veins in the foot, neck, elbow, or other such target vein sites.

In this example the electronic circuitry 20 of the signal generator 10 further includes output circuitry 56. The output circuitry operates to convert the square wave signal generated by the oscillator 52 into a desired output signal, such as having a waveform shown in one of FIGS. 7-9.

The first stage 58 of the output circuitry includes electronics including operational amplifiers 64 and 66, and a capacitor 68. The first stage 58 is coupled to the variable control 54 to receive the input from a user to adjust the magnitude of the signal generated by the signal generator 10. In this example, the variable control 54 is a potentiometer that provides a variable resistance. The variable control 54 is electrically coupled to an input of the operational amplifier 64. The voltage of the signal provided by the variable control 54 changes the variable control is adjusted. The operational amplifier 64 is configured as a unity gain buffer amplifier in this example. In some embodiments the variable control operates to adjust the magnitude of an output voltage so that magnitude is adjustable from 0 volts to 40 volts. In some embodiments the maximum output voltage is within +/−10% of 40 volts. Other embodiments have other ranges of output voltages. In some embodiments the current delivered depends on the patient's natural electrical resistance, the surface area stimulated, and other factors such as the conductivity of the connecting medium (e.g., water, vs gel), self adhesive electrodes, amount of oil on skin, capacitance of the patient, and other technical/anatomical factors such as dehydration and the stress level of the patient.

The oscillator 52 generates a square wave output (e.g., pin 7) that is then supplied to the capacitor 68. The capacitor 68 converts the square wave signal to a series of pulses having a leading edge with a sharp voltage transition, followed by a trailing edge in which the voltage tapers off. The signal is then provided to the second stage 60 where it is further filtered and amplified such as using the amplifier including operational amplifier 66 arranged in a non-inverting configuration.

The amplified signal is then provided to the second stage 60, including the transformer 70, which operates to amplify and rectify the signal.

In some embodiments the transformer 70 has an unequal ratio of windings. As one example, the transformer is a 10:1 transformer, which is arranged in a step-up configuration to increase the voltage at the output. In other possible embodiments the transformer can be arranged in a step-dawn configuration. Other embodiments have other ratios of windings. The output can also be generated in the second stage without using a transformer in yet other embodiments.

In this example, the transformer 70 is a center tap transformer. The oscillating signal generated by the first stage 58 is provided to the primary winding and the center tap, and operates in conjunction with a pair of diodes to rectify the output signal. The output signal is generated at the secondary windings and supplied to the output terminal 16. The ratio of the primary windings to the secondary windings determines the amplification provided by the transformer 70.

In some embodiments the circuitry 20 further includes electronic components, and/or programming, that are configured to automatically vary the output signal, which may include varying one or more of the output voltage, the output current, shape of the output voltage waveform, and/or frequency of the output signal over time, without having to adjust the variable controls (e.g., potentiometers 22, 24). In one embodiment, the output signal may be changed over time by executing specific computer code or a software program in the microprocessor. In another embodiment, the output signal may be randomly changed inexpensively by the inclusion of a typical flashing light emitting diode (LED) 63 within the circuitry of the signal generator 10. Flashing LEDs automatically blink when supplied with electrical power, alternating between an "on" and "off" state, with the frequency of flashing between the two states depending on the input voltage. In one embodiment, the flashing LED is placed in the electronic circuitry downstream of the microprocessor and upstream of the amplifying circuit that is connected to the output leads that are attached to the patient by the electrodes. The flashing LED, oscillating between an "on" and "off" state, is constantly switching the output current on and off, causing the signal generator 10 to vary the electrical output signal and voltage over time, according to the flashing frequency of the flashing LED. In this manner, the LED acts as a repetitive timer for the output signal from the signal generator. And because the frequency of the LED is dependent on its input voltage, adjusting the voltage from the potentiometer will change the frequency of the flashing LED, so as to provide an infinitely variable output signal to the patient.

Furthermore, the lower the quality of the components used to make the flashing LED, as with inexpensive flashing LEDs, the more variation or randomness there will be in the consistency or stableness of the frequency of the flashing for a given voltage. Accordingly, lower quality flashing LEDs provide a flashing pattern that is more random than that of higher quality flashing LEDs. Therefore, in one embodiment, to achieve more randomness in the frequency of the electrical signal sent to the patient from the signal generator 10, it may be beneficial to use lower quality flashing LED within the circuitry as disclosed herein.

In still alternate embodiments, additional methods to vary the output signal and voltage over time are contemplated herein, without departing from the scope of the present disclosure. By varying the output signal in the manner disclosed herein, the patient's body is constantly reacting to the changing output signal, rather than possibly becoming accustomed to a constant output signal to which the venous system might otherwise no longer respond after a short exposure thereto.

The signal generator 10 may also include at least one indicator 32, such as an LED or other lighted indicator, to indicate to the medical practitioner utilizing the electrical stimulation apparatus 1 as to when the power to the apparatus is turned "on." An additional indicator may be included to indicate when the electrical signal is being sent to a patient. In one embodiment, the indicator may perform both functions, however, in alternate embodiments, separate indicators may be utilized to communicate each of the two functions.

The apparatus 1 may also include programming and/or a display screen configured to communicate and display for the medical practitioner the real time output voltage and signal, an initial set output voltage and signal, fault conditions, stimulation apparatus fault diagnostic information, or any other such setting, output, or feedback information as may be desired. In another embodiment, the apparatus 1 may include a display configured to graphically display the real time electrical information (e.g. the electrical signal and/or voltage vs. time) being sent to the patient. In still further embodiments, the stimulation apparatus 1 may include data output programming and associated output connectors that are configured to permit the apparatus to be connected to a separate, stand-alone external display for displaying any/all of the information disclosed herein.

In some embodiments the electronic circuitry 20 is arranged on one or more circuit boards. The circuit boards include at least one substrate layer, and typically have at least one layer of electrical traces formed thereon to make electrical connections between the electronic components. In some embodiments the electronic signal generator 10 is formed on the circuit board.

The output signal is sent from the signal generator 10 to the patient's body by two electrical leads 26 that are connected at a proximal end to the signal generator 10, and at a distal end to a pair of electrodes 18. In one embodiment of the present disclosure, the electrodes 18 may be configured as a pair of cups or other containers 28, such as for example, a pair of manicure nail soaking bowls or other such similar containers, that are configured to hold a liquid electrolyte solution 30 into which at least some of the finger and thumb tips (or more) of a patient are to be submerged. In some embodiments the electrodes are connected to or otherwise associated with the containers 28, such as being fastened to an interior of the container by an adhesive or molded into the container. The electrodes can also be placed into the container without being securely fastened to the container in some embodiments. In some embodiments the container is conductive, such that the container functions as an electrode. In some embodiments the containers include one or more recessed regions sized and shaped to receive at least the tips of the fingers of a hand, or the toes of a foot, therein. The purpose of suing an electrolyte solution is to provide a conductive liquid medium into which the patient may place his fingers and through which the electrical signal may be delivered to the patient. In one embodiment, the electrolyte solution may be a mix of minerals and water. However, in alternate embodiments, the electrolyte solution may be any other type of solution used for increasing electrical conductivity between the electrical leads and the skin of a patient.

While a previous embodiment disclosed the electrodes configured as small containers for permitting the fingertips to be placed into an electrolyte solution, the electrodes should not be limited to such embodiment and in alternate embodiments may have alternate configurations as desired. For example, in alternate embodiments, the electrodes may be alternate sized containers that permit the submersion of a patient's full hands, feet, or any portion of the patient's body, including but not limited to arms and/or legs, into an electrolyte solution in electrical communication with the signal generator. In still alternate embodiments, the electrodes may be configured as a pair of conductive electrode pads having a conductive gel or adhesive layer disposed on one side thereof to help adhere the electrode pad to the skin of a patient and to aid in making good electrical contact between the conductive pad and the patient's skin. Such electrode pads may be similar to those used with transcutaneous electrical nerve stimulation (TENS) devices or portable defibrillators. Furthermore, in still alternate embodiments, the electrodes may be one or more of a metal pin-type probe or metal plate that are contact based electrodes. In still alternate embodiments, the electrode may be a finger clamp-type probe that is similar in mechanical structure to those used to measure pulse oximetry. In yet additional embodiments, the electrodes may be conductive garments, or other such contact-based electrode having an alternate physical configuration, without departing from the scope of the disclosure herein. In yet an additional embodiment, the electrodes may be configured as one or more electromagnets that generate a magnetic field, into which magnetic field the patient may place his hands, feet, or limbs. The electromagnetic field is configured to generate a complementary electric signal in the patient's body via changes to the magnetic field. In such an embodiment, the patient is not directly connected to the signal generator.

In one embodiment, the electrical signal output from the signal generator 10 sent to a patient's limbs through the electrodes includes an electrical signal that is an alternating signal (AC). In one embodiment, the AC signal sent to the patient has a frequency of 7.83 Hz (or 7.83 full alternating cycles per second). This means that the output circuit is interrupted 7.83 times per second. This frequency of 7.83 Hz has been selected in one embodiment to provide the nerves of the patient time to repolarize between successive output signals, and thus have time to get prepared for the next subsequent output signal. By providing adequate time to allow the nerves to repolarize, the signal generated by the signal generator 10 has a consistent effect on the skin, nerves, and muscles in the vicinity of the electrodes.

However, while the above embodiment operates at a frequency of 7.83 Hz, the frequency of the output signal should not be read to be limited only to such specified frequency, and in alternate embodiments, the AC or DC signal may have a different frequency without departing from the scope of the present disclosure. In alternate embodiments, the frequency of the output signal may be any alternate frequency, depending on the specific circuitry design of the signal generator. For example, in an alternate embodiment, a different duty cycle or output cycle, or even a different waveform that is subsequently developed, may use a different frequency. Furthermore, in alternate embodiments, the signal generator 10 may be configured to adjust the frequency or waveform of the output signal based on sensed feedback related to the physiological differences between patients of different ages, the patient's circulatory system patency, and other biomedical and/or bioelectrical aspects of the patient's body. In one embodiment, the microprocessor in the signal generator 10 may further contain programming that adjusts the output signal for the changes that are usually associated with an aging patient, such as thinner skin, more sensitive skin, skin that is sensitive to bleeding, etc.

In one embodiment, the output voltage from the signal generator 10, which is set by at least one of the potentiometers 22, 24, is initially set to be within the range of between 0 volts and 90 volts. In another embodiment, each of the two output voltage channels may be set to be within the range of between 0 volts and 90 volts. However, in alternate embodiments, the potentiometers 22, 24 may have larger or smaller output voltage ranges than that disclosed herein, and may each be selectably set to an initial output voltage value, or adjusted to a new output voltage value, within such larger or smaller voltage ranges, without departing from the scope of the present disclosure.

Feedback System.

The signal generator 10 may further include an integrated feedback system that is configured to measure the resistance and capacitance of the patient's body during the time between each successive cycle of the output signal. In one embodiment, the feedback system utilizes a ten to one (10:1) audio transformer that responds to the electrical and capacitive resistance (i.e., electrical back pressure) of the patient's body, as well as any changes thereto, in order to adjust the output signal sent to the patient. Each human body presents with an electrical resistance. This resistance can change with the body's weight, hydration, etc. This electrical resistance can also change during the treatment. The signal generator 10 uses the audio transformer to measure the electrical resistance of the patient's body and, in response, appropriately alter the output voltage and/or current transmitted to the patient as part of the signal. In doing so, the signal may be altered based on the feedback from the feedback system to ensure that the signal generator 10 is eliciting the same clinical or physiological response in the patient's body, even when the patient's bodily response to treatment is changing (i.e. changes to the patient's electrical back pressure, or bodily resistance and/or capacitance).

A simple transformer performs the job of monitoring the electrical back pressure of the patient's body simply and inexpensively. When the microprocessor, via the transformer electrical communication with the patient, detects a very high electrical resistance in the patient's body, then very little current will flow from the signal generator into the patient for a given constant output voltage from the signal generator to the patient. If the input current from the signal generator is very low (as when powered by a small battery), and if the output voltage leads do not have much resistance, then the battery power decreases and the current drops significantly. The measured electrical resistance of the human body is fairly constant, but the capacitance of the human body can vary greatly. This is a concern, because the sudden release or electrical energy or charge from the capacitor-like parts of the human body can result in the body receiving a painful jolt of electricity that may potentially cause damage to the patient's nervous or cardiac system, and otherwise interrupt the desired clinical response in the patient's body caused by the treatment.

The transformer of the feedback system filters an output voltage of the signal generator, which voltage fluctuates over time according to a preprogrammed voltage waveform, to allow the specific portions of the voltage waveform that are the most effective at eliciting the desired vein distension response to pass through to the patient. The electrical back pressure in the patient causes a reaction in the patient's body that creates a resulting electrical signal from the patient's body that can be captured and read by the signal generator, which can then be used as an input to adjust the output voltage of the next cycle of the output signal from the signal generator.

In alternate embodiments, the feedback mechanism may be specific programming within the microprocessor of the signal generator that is configured to monitor the feedback of the patient's electrical resistance and capacitance and, in turn, adjust the output signal sent to the patient based on the monitored feedback. In still alternate embodiments, the feedback system may utilize a plurality of sensors configured to measure the patient's resistance and capacitance, or any other such electrical component or computer code configured to measure feedback resistance and capacitance, without departing from the scope of the present disclosure.

In one embodiment, the apparatus 1 can be configured to stop all output signals from the signal generator 10 and wait for the patient's body to react to the last output signal. When the patient's body reacts to the last signal, the patient's body produces a resulting electrical signal that can be captured by the signal generator 10, analyzed, and used to alter the next output signal from the signal generator 10 that is sent to the patient. This can be done in real time with the appropriate microprocessor and software. In an alternate embodiment, if the feedback mechanism of the signal generator measures a change in a patient's bioelectrical resistance or capacitance of more than 10% between successive cycles of the output signals, the signal generator is configured to shut off or go into a fault mode, as a change of larger than 10% may indicate that the patient's body is experiencing a stress response and no is longer responding to the output signals. In one embodiment, the signal generator would automatically adjust the output signal waveform, voltage, and current based on the individual patient's specific physiology and related bioelectrical properties.

In still further embodiments, the signal generator includes software to collect physiological data from the patient using the stimulation apparatus, including the patient's physiological response data. That data can then be stored and analyzed by the signal generator and used to change the output signal in real time, so as to optimize the output signal and the achieved venous response for the specific patient.

Included in the signal generator may be a microprocessor having programming therein configured to control the amount of current and voltage being sent to the patient via the electrodes, as well as the shape of the output voltage waveform that is being sent to the patient, monitor the electrical feedback received from the patient (i.e. the patient's internal bodily resistance and capacitance), and automatically adjust, in real time, any of the voltage output, the current output, or the shape of the voltage waveform being sent to the patient. The microprocessor may be any programmable microprocessor having any speed or internal memory size without departing form the scope of the present disclosure. In one embodiment, the microprocessor may include a comparator circuit configured to compare the original output signal sent to the patient from the signal generator to the returned signal from the patient. The results of the comparison are then used by the microprocessor to change the output signal proportionately to balance the next output signal sent to the patient. In such an embodiment, the microprocessor may have a baseline waveform stored in its memory which is sent to the patient with the first signal. A response/reflect signal is then sent back to the microprocessor from the patient through the feedback system, which response/reflex signal is also stored in the microprocessor. Thereafter, the microprocessor adapts the next outgoing signal based on the prior stored incoming response/reflex signal to gently coax the patient's nerves to carry the best waveform, voltage, and current necessary to produce the greatest visible presentation of the vein. This comparative process ensures that the output signal being set to the patient each time will continue to elicit the desired physiological and clinical response in the peripheral veins of the patient, preventing the patient's body from getting accustomed to the signal being sent.

Furthermore, the processor includes programming configured to maintain a predefined signal frequency. For example in one embodiment, the microprocessor is programmed to maintain a preprogrammed signal frequency of 7.83 Hz. However, in alternate embodiments, alternate frequencies may be chosen without departing from the present disclosure. For example, in some patient groups or subsets, such as obese patients, geriatric patients, or neonatal patients, alternate signal frequencies may be needed to aid in eliciting the optimal venous presentation results. In addition, in an embodiment, the microprocessor may be programmed and configured to continue to operate properly on a constantly declining voltage, such as for example when the power supply is a battery that slowly runs out of power over time and continued use.

Waveform Graph

Figure 7:
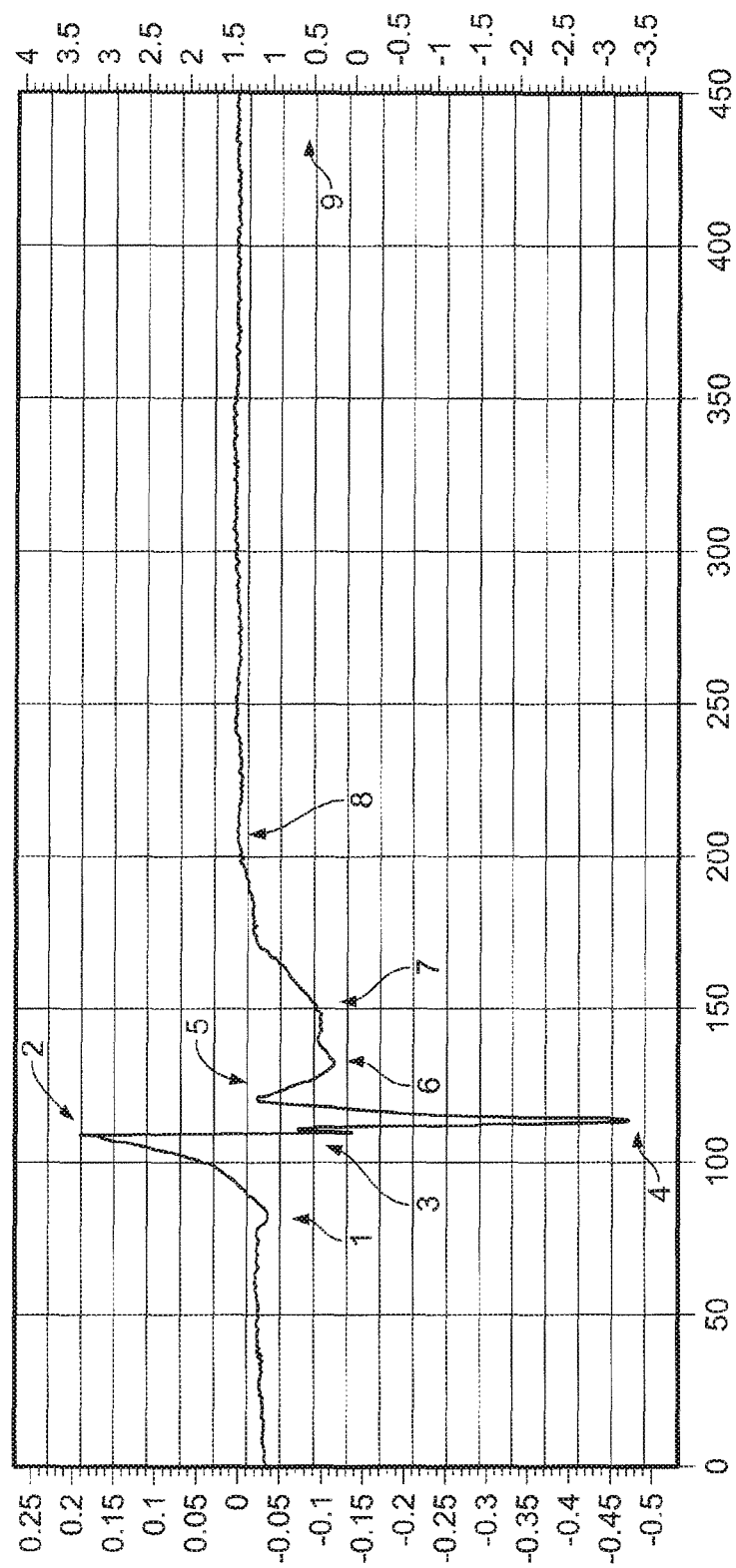
FIG. 7 is a waveform graph of the output voltage vs. time for one cycle of the output signal, such as generated by the signal generator shown in FIG. 6.

FIG. 7 shows an exemplary graph of an embodiments of active portions of a single cycle of a signal. The graph shows an output voltage (the Y-axis) of the output signal, versus time in milliseconds (the X-Axis), that is able to illicit the desired vein distension and pain suppression response in a patient. The shape of the signal, including the location and amplitude of the various peaks and valleys therein, is an exemplary waveform that is able to elicit active, signal-based enlargement of the target peripheral veins, which aids in the performing of venipuncture by medical practitioners, for example.

Referring further to FIG. 7, a plurality of points 1-9 are identified on the graphed waveform showing the output signal's output voltage vs. time. Point 1 on the graph corresponds to the beginning of a new cycle of the repetitive output signal, and indicates the initial output voltage from the signal generator that is selected to alert or stimulate a patient's sensory nerve (via its dendrites in the surface of the skin) to a change in condition. This initial output voltage initiates a tiny electrical signal in the patient's body, having a unique voltage, current, and waveform, to be sent to the central nervous system so the brain can monitor the extremities. In response, the brain sends a healing signal back to that specific sensory dendrite from which the signal to the brain originated.

Point 2 on the graph corresponds to the primary effective portion of the nerve stimulation signal. This point is the main output voltage in the nerve stimulating portion of the output signal that causes the peripheral nerves in the patient's limbs to over-react and causes a simultaneous tetany or contraction of the nearby muscles surrounding the target peripheral veins. This is the portion of the waveform that is adjusted via the knob of one of the potentiometers 22, 24 on the signal generator. In overweight patients, the voltage level at Point 2 is automatically suppressed by a layer of fat in the skin. Accordingly, for overweight patients, in order to get the signal to reach the nerves of the patient and overcome the resistance of the fat layer, it may be necessary to send a higher output voltage to the patient. This can be accomplished by using a ten to one (10:1) audio transformer, or other such transformer, in the signal generator to amplify the output voltage signal sent to the patient. Alternatively, the increasing of the voltage to overcome the resistance of the fat layer so the signal may reach the nerves may also be accomplished by the implementation of programming contained in the microprocessor.

Point 3 in the voltage waveform graph corresponds to the output voltage that triggers the sensory nerve in the patient to "turn of" In this regard, Point 3 is the voltage that triggers the nerve to be at rest and reset to its standby voltage, waiting to be used or triggered "on" again in the next subsequent cycle of the output signal. Point 4 in the voltage waveform graph is the output voltage that cancels the positive portion of the signal and balances the stimulation apparatus' nerve signal to allow the nerve time to reset itself, or repolarize.

Point 5 in the waveform graph corresponds to the muscle stimulation portion of the output signal, and is the output voltage that causes the muscles to stimulate the venous muscle pump that in turn causes the veins to distend and fill with blood. In the waveform presented in FIG. 7, the length of time during which this portion of the signal is active is small, however in some patients the length of time over which this portion of the output voltage in the output signal is active will be adjusted to achieve the proper amount of motor muscle stimulation to activate the venous muscle pump. The longer that this portion of the signal is active, the more that the muscles are stimulated. In addition, the small muscles surrounding the veins require a different amount of active stimulation time to activate the venous muscle pump action than that of the larger muscles. This portion of the waveform also may be adjusted from patient to patient to achieve the optimal venous muscle pump action in each patient.

Point 6 in the waveform graph is the point at which the motor muscle stimulation is shut off to allow them to reset and get ready for the next cycle of the signal. Point 7 in the waveform graph corresponds to a reflex signal back pressure from the patient's peripheral nervous system, indicating that the nervous system is trying to take over control of the nerves and muscles and stabilize the patient's muscle and nerve activity. Point 8 in the waveform graph corresponds to a period of zero output voltage to the patient, and is part of the integrated feedback loop that the peripheral nervous system uses to gently restore the patient's baseline electrical potential back to its original resting electrical potential, or internal voltage. In comfortable, relaxed patients, their resting potential, or measured voltage, may be on the order of 20 millivolts. However, in some patients who are anxious, their measured resting potential may be zero volts, or a positive measured voltage, which are otherwise higher electrical potentials or voltages than a typical relaxed patient. This initial resting potential measurement is used to setup the basic parameters of the first and each succeeding treatment output signal from the signal generator.

Point 9 in the waveform graph corresponds to the patient's baseline condition, whereby there is no active output signal or voltage being sent to the patient's body, and the patient is otherwise unaffected by any output signal from the stimulation apparatus. This also corresponds to the period during which the signal generator is monitoring the patient's internal electrical potential and preparing to initiate a new cycle of the signal, and adjusting the active portion of the output signal based on the feedback monitored from the patient.

Figure 8:
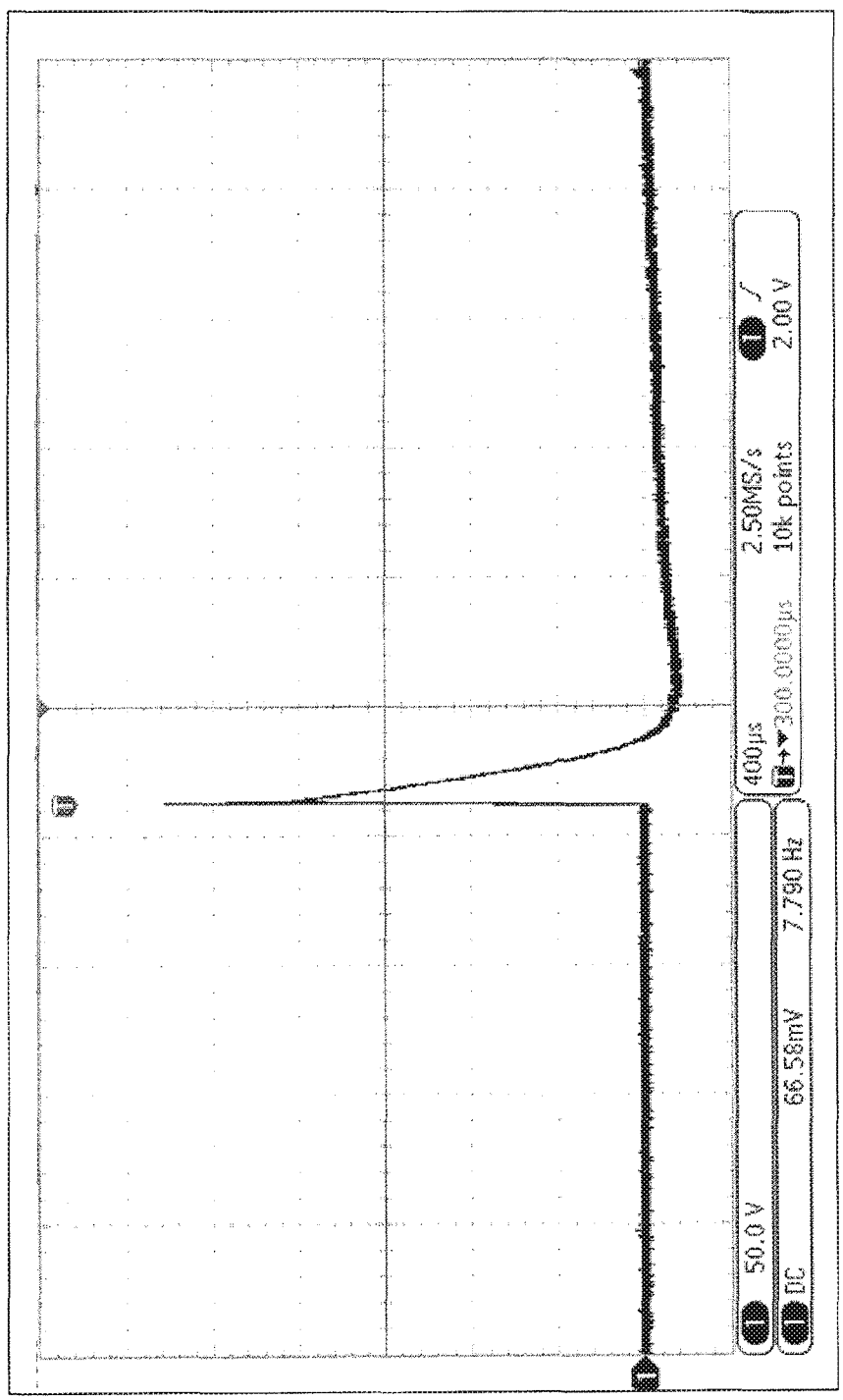
FIG. 8 is a waveform graph illustrating another example waveform.
Figure 9:
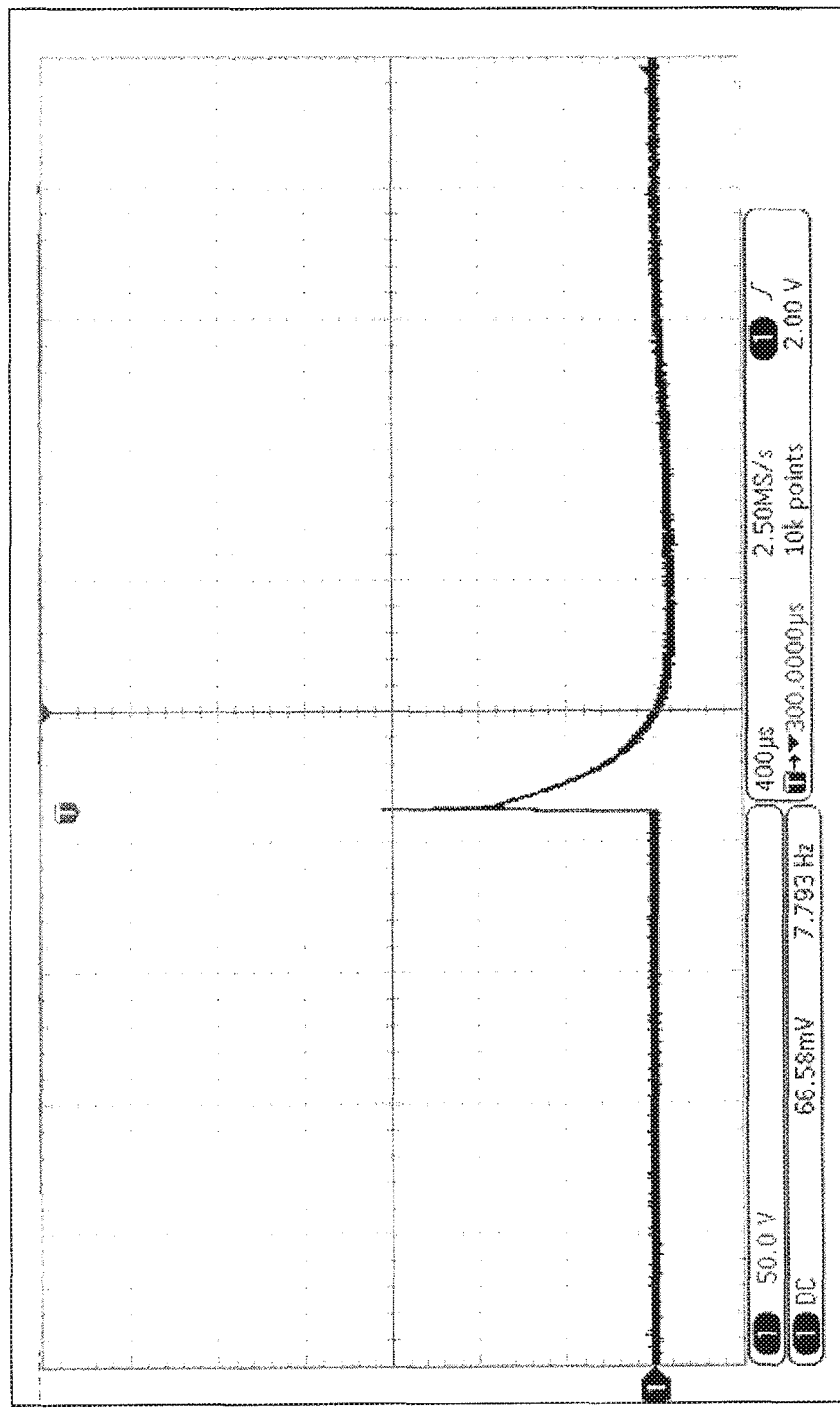
FIG. 9 is a waveform graph illustrating another example waveform.

FIGS. 8-9 illustrate other example waveforms that can be used in other embodiments, or with different subjects due to different characteristics of the subjects.

In some embodiments, the waveform has one or more of the following properties. The highest voltage reached stimulates the muscles surrounding the veins. The width of the signal from the baseline until the return the baseline stimulates the nearby voluntary motor muscles to function as a venous muscle pump to empty the adjacent veins of blood. The return to baseline stops the action of both muscles. The negative pulse following the first return to baseline begins the return to the original resting state of the muscles and nerves. The negative pulse delivers a negative polarity pulse that with a volume of energy (e.g., watts) that equals the energy delivered in the original positive polarity phase. The second return to baseline finishes the polarity balancing. The time period until the next signal allows the nerve and muscle cells to re-organize and prepare for the next sequence of stimulation. Other waveforms have other properties.

Apparatus Operation and Stimulation Action

In operation, the stimulation apparatus functions as follows. The electrodes are placed in electrical contact with the fingers or hands of a patient. In one embodiment, this involves the patient placing the fingertips of each hand into separate containers of an electrolyte solution. The electrolyte solution in each container is placed in electrical communication with the signal generator by separate electrical leads that are terminated at one end in the electrolyte solution, and at the opposite end to output contacts of the signal generator. In alternate embodiments, the electrodes may be adhesive backed pads that are affixed directly to the patient's skin.

The power source supplies power to the signal generator. The medical practitioner adjusts the output voltage to the patient by rotating an adjustment knob of at least one of two potentiometers. The signal generator is switched "on" and the preprogrammed electrical output signal is transmitted through the leads and electrodes to the fingertips, hands, and arms of the patient. The preprogrammed output signal includes a repetitive cycle of preprogrammed fluctuating output voltages at various specified points in time for each cycle. In one embodiment, the initial output voltage may be set between 0 and 90 volts and the signal delivered is less than one milliamp. However, in alternate embodiments, the output voltage range may be larger or smaller, or cover a different voltage range than that disclosed in the present embodiment, and the output signal may be larger than 1 milliamp without departing from the scope of the present disclosure.

Each cycle of the output electrical signal includes a period of active output voltage and a period of rest, where no output voltage is being imparted to the patient's limbs. The preprogrammed output voltage includes several phases including: an initiation phase that alerts the patient's sensory nerve to the presence of the output voltage; a primary nerve stimulation phase that causes the peripheral nerves to force the motor muscles surrounding the peripheral target veins to contract; an end to the nerve stimulation phase that turns "off" the sensory nerve; a balancing phase that cancels the stimulation signals that were sent to the nerves to allow the nerves to reset; a muscle stimulation phase that activates the venous muscle pump; a shutdown phase that ends the activation of the muscles; an electrical back pressure phase; an electrical feedback phase; and a rest phase with no active voltage output to allow the patient's system time to reset before the next cycle begins. This cycling part of the waveform used in some embodiments is not required in all embodiments. Other embodiments utilize other waveforms that cause one or more of the actions described herein. Additionally, suitable waveforms may vary relative to the patient's physiology, the design and limitations of the electronic circuitry, and/or the method used to deliver the signals to the patient.

The result of the repetitive electrical cycles in the output signal that are imparted to the patient is a physiological response in the patient as follows. One portion of the generated electrical signal stimulates the muscles near the electrodes to contract and relax. These muscles are circular in nature and when they contract they form a tube. This tube is larger than normal and creates a vacuum which can have the effect of drawing in whatever blood is available via the capillaries and the nearby arteries. In addition, part of the waveform stimulates the adjacent muscles which act as a venous muscle pump to increase the local blood pressure in the veins, thus adding more blood to the now visually obvious and distended veins. This venous muscle pump is the body's way of moving blood from the arteries and capillaries back to the heart. The multitude of valves present in the veins prevent retrograde blood flow, thus aiding the enlarging of the target veins internal volume for easier access for venipuncture. For some patient groups, such as geriatric patients, this venous muscle pump action may be further aided in conjunction with the presently disclosed electrical venous stimulation apparatus, by the use of a tourniquet applied between the target vein and the heart.

The electrical venous stimulation apparatus of some embodiments works best to present the veins in the back of the hands, top of the feet, and the forearms.

In embodiment, the electrical venous stimulation apparatus further operates as a TENS device in that there is a portion of the output voltage waveform that is configured to numb the tissue adjacent the electrodes (and accordingly the target vein site). This included functionality makes the process of inserting a needle into a target vein while using the electrical venous stimulation apparatus less painful to the patient when the needle stick actually occurs. In embodiments having two potentiometers, the second potentiometer controls the output voltage channel that creates the TENS device functionality. The second output channel can be configured to attach directly on the skin of the patient nearby the projected needle stick site to focus the numbing effect to a specifically local area. The second channel can be configured to perform this nerve deadening functions specifically. Thus in one embodiment, one output voltage channel is used to achieve the displaying of an enlarged, engorged vein, and the other output voltage channel is used to numb the area of the needle stick.

Figure 5:
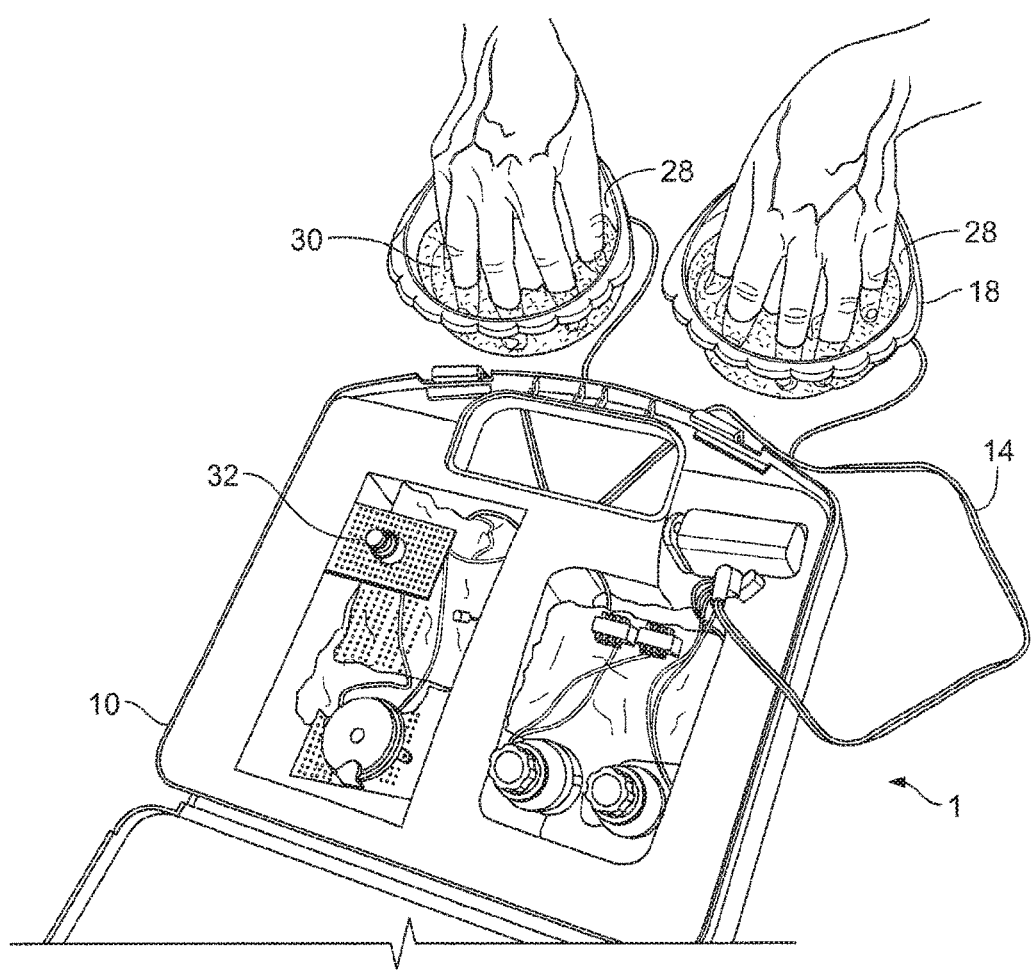
FIG. 5 is a another top front isometric view of the electrical vein stimulation and expansion apparatus of FIG. 1, showing the apparatus in use and illustrating the distending and protruding of the patient's veins.

The apparatus of the present disclosure is configured to non-invasively alter the physiology of the peripheral veins that are targeted for venipuncture in the limbs of a patient using an active electrical signal, rather than using passive means traditionally used, or requiring the use of a tourniquet. In an aspect of the present disclosure, an active signal imparted to the skin of a patient by the apparatus elicits a physiological response and a change in condition/behavior of the target vein, causing the vein to fill with blood and become distended/enlarged and become more rigid and therefore easier to visualize under the skin, as shown in FIG. 5 during and after the electrical stimulation (compare with FIG. 4, which illustrates the hands before the electrical stimulation). In this manner, using such an apparatus and methodology as disclosed herein, it becomes easier for medical practitioners to locate the target vein and achieve successful and proper venipuncture. No other active device currently exists that non-invasively changes the physiology of the tissue in and around the target veins to aid in locating the target vein and increasing the ease of achieving successful and proper venipuncture without the need for multiple attempts.

As discussed herein, one embodiment is a method of accessing a vein of a person, the method comprising: receiving a portion of a limb of the person into a container; supplying a liquid electrolytic solution into the container, wherein the liquid electrolytic solution is in contact with the portion of the limb; electrically stimulating the portion of the limb with at least one signal generated by an electrical signal generator, the electrical signal provided to the electrolytic solution by at least one electrode in contact with the liquid electrolytic solution; causing at least one vein in the limb of the person to distend in response to the electrical stimulation; and inserting a tip of a needle into the vein while it is distended to access the vein.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. An electrical venous stimulation apparatus for causing a target vein in a subject to enlarge and fill with blood under a surface of the subject's skin to enhance identification of suitable veins for cannulation, the electrical venous stimulation apparatus comprising:
    a power supply;
    a signal generator powered by the power supply, the signal generator configured to generate an electrical output signal;
    multiple electrodes in electrical communication with the signal generator and configured to be placed in electrical communication with the subject at different locations; and
    wherein the electrical output signal includes an output voltage, electrical current, and a waveform that changes with time in a preprogrammed repeating cycle, the output voltage, electrical current, and waveform being configured to elicit a physiological response that non-invasively alters a physiology of a target vein, wherein the target vein is caused to enlarge and fill with blood under the surface of the subject's skin, wherein the waveform comprises:
        a first phase in which a positive polarity pulse above a baseline voltage is delivered;
        a second phase in which a negative polarity pulse below a baseline voltage is delivered; and
        a third phase in which no voltage is delivered for a time period prior to a next sequence of stimulation.

2. The electrical venous stimulation apparatus of claim 1, further comprising a first of the electrodes being configured to provide the electrical output signal to a limb of the subject, and a second of the electrodes being configured to provide the electrical output signal to the limb of the subject or a second limb of the subject.

3. The electrical venous stimulation apparatus of claim 1, wherein the output voltage, electrical current, and waveform are further configured to suppress pain signals at a venous needle stick site of the subject.

4. The electrical venous stimulation apparatus of claim 1, wherein the second phase comprises:
    a first stage in which a first portion of the negative polarity pulse is delivered;
    a first return to the baseline voltage;
    a second stage in which a second portion of the negative polarity pulse is delivered; and
    a second return to the baseline voltage.

5. The electrical venous stimulation apparatus of claim 1, wherein energy delivered in the first phase is balanced by energy delivered in the second phase.

6. The electrical venous stimulation apparatus of claim 1, wherein the signal generator is programmed to:
    measure, during the third phase, a resting potential of the subject; and
    prepare the next sequence of stimulation based on the resting potential.

7. The electrical venous stimulation apparatus of claim 1, wherein the signal generator is programmed to:
    monitor biological electrical feedback based on electrical resistance and capacitance of the subject;
    compare the biological electrical feedback from the subject with a transmitted output signal; and automatically adjust subsequent output signals to be sent to the subject based on the comparison between the transmitted output signal and the biological electrical feedback.

8. The electrical venous stimulation apparatus of claim 1, wherein a highest voltage reached stimulates muscles surrounding the target vein.

9. The electrical venous stimulation apparatus of claim 1, wherein the negative polarity pulse causes a return to a resting state of muscles.

10. The electrical venous stimulation apparatus of claim 1, wherein the negative polarity pulse is delivered with a power that equals the power delivered with the positive polarity pulse.

11. The electrical venous stimulation apparatus of claim 1, wherein the electrical output signal is an AC signal with a current of less than one milliamp and a frequency of between 4 and 12 Hz, and the output voltage is between 0 and 90 volts.

12. The electrical venous stimulation apparatus of claim 1, wherein the target vein is caused to distend under the surface of the subject's skin.

13. The electrical venous stimulation apparatus of claim 1, further comprising electrical leads configured to provide the electrical output signal generated by the signal generator to the electrodes, each of electrical leads connecting a respective one of the electrodes to the signal generator.

14. The electrical venous stimulation apparatus of claim 1, further comprising a variable control configured to adjust a magnitude of the output voltage.

15. The electrical venous stimulation apparatus of claim 1, wherein a magnitude of the output voltage is variable from about 0 to about 40 volts.

16. The electrical venous stimulation apparatus of claim 1, wherein the signal generator further comprises:
   a power switch;
   an oscillator including an integrated circuit;
   a variable control configured to adjust a magnitude of the output voltage in response to an input; and
   output circuitry comprising:
      a first stage including operational amplifiers and a capacitor; and
      a second stage including a center tap transformer.

17. The electrical venous stimulation apparatus of claim 1, wherein each of the electrodes comprises an electrode pad having an adhesive layer disposed on one side thereof.

18. The electrical venous stimulation apparatus of claim 1, wherein the different locations include locations on a limb of the subject.

19. The electrical venous stimulation apparatus of claim 1, wherein one of the different locations is the palm of the subject.

20. The electrical venous stimulation apparatus of claim 1, wherein one of the different locations is the bicep of the subject.

21. A method of stimulating a vein in a subject by causing a target vein in a subject to enlarge and fill with blood under a surface of the subject's skin to enhance identification of suitable veins for cannulation, the method comprising:
   placing multiple electrodes in electrical communication with the subject at different locations; and
   generating an electrical output signal including an output voltage, electrical current, and a waveform that changes with time in a preprogrammed repeating cycle, the output voltage, electrical current, and waveform being configured to elicit a physiological response that non-invasively alters a physiology of a target vein, wherein the target vein is caused to enlarge and fill with blood under the surface of the subject's skin, wherein the waveform comprises:
      a first phase in which a positive polarity pulse above a baseline voltage is delivered;
      a second phase in which a negative polarity pulse below a baseline voltage is delivered; and
      a third phase in which no voltage is delivered for a time period prior to a next sequence of stimulation; and
   transmitting the electrical output signal to the subject via the multiple electrodes.

22. The method of claim 21, wherein placing the multiple comprises placing a first of the electrodes at a limb of the subject and a second of the electrodes at the limb of the subject or a second limb of the subject.

23. The method of claim 21, wherein the transmitting comprises suppressing pain signals at a venous needle stick site of the subject.

24. The method of claim 21, wherein the second phase comprises:
   a first stage in which a first portion of the negative polarity pulse is delivered;
   a first return to the baseline voltage;
   a second stage in which a second portion of the negative polarity pulse is delivered; and
   a second return to the baseline voltage.

25. The method of claim 21, wherein energy delivered in the first phase is balanced by energy delivered in the second phase.

26. The method of claim 21, further comprising:
   measuring, during the third phase, a resting potential of the subject; and
   preparing the next sequence of stimulation based on the resting potential.

27. The method of claim 21, further comprising:
   monitoring biological electrical feedback based on electrical resistance and capacitance of the subject;
   comparing the biological electrical feedback from the subject with a transmitted output signal; and
   automatically adjusting subsequent output signals to be sent to the subject based on the comparison between the transmitted output signal and the biological electrical feedback.

28. The method of claim 21, wherein a highest voltage reached stimulates muscles surrounding the target vein.

29. The method of claim 21, wherein the negative polarity pulse causes a return to a resting state of muscles.

30. The method of claim 21, wherein the negative polarity pulse is delivered with a power that equals the power delivered with the positive polarity pulse.

31. The method of claim 21, wherein the electrical output signal is an AC signal with a current of less than one milliamp and a frequency of between 4 and 12 Hz, and the output voltage is between 0 and 90 volts.

32. The method of claim 21, wherein the transmitting comprises causing the target vein to distend under the surface of the subject's skin.

33. The method of claim 21, further comprising adjusting a magnitude of the output voltage according to an input received at a variable control.

34. The method of claim 21, wherein a magnitude of the output voltage is variable from about 0 to about 40 volts.

35. The method of claim 21, wherein a tourniquet is applied subsequent to the stimulation.

36. The method of claim 35, wherein peripheral intravenous cannulation is performed on the subject subsequent to the stimulation.

\* \* \* \* \*